United States Patent [19]

McKinney

[11] Patent Number: 5,087,723
[45] Date of Patent: Feb. 11, 1992

[54] HYDROCYANATION OF CONJUGATED 2-ALKENOATES

[75] Inventor: Ronald J. McKinney, Wilmington, Del.

[73] Assignee: E. I. du Pont de Nemours and Company, Wilmington, Del.

[21] Appl. No.: 517,135

[22] Filed: May 1, 1990

[51] Int. Cl.$^5$ ............................................ C07C 253/10
[52] U.S. Cl. ...................................... 558/338; 558/341
[58] Field of Search .......................... 558/338; 508/341

[56] References Cited

U.S. PATENT DOCUMENTS

| | | | |
|---|---|---|---|
| 2,571,099 | 10/1951 | Arthur, Jr. et al. | 558/338 X |
| 3,496,215 | 2/1970 | Drinkard et al. | 558/338 |
| 3,496,217 | 2/1970 | Drinkard, Jr. et al. | 558/338 |
| 3,496,218 | 2/1970 | Drinkard, Jr. et al. | 558/338 |
| 3,564,040 | 2/1971 | Downing et al. | 558/335 X |
| 3,852,325 | 12/1974 | King | 558/355 |
| 3,865,865 | 2/1975 | Musser | 558/465 |
| 3,925,445 | 12/1975 | King et al. | 558/338 |
| 4,774,353 | 9/1988 | Hall et al. | 558/335 |
| 4,874,884 | 10/1989 | McKinney et al. | 558/338 |

OTHER PUBLICATIONS

Druliner, J. D., Mechanistic Studies of Nickel Catalyzed Addition of DCN and H$^{13}$CN to Pentenenitriles, Organometallics (1984) 3, pp. 205–208.

*Primary Examiner*—Joseph Paul Brust

[57] ABSTRACT

An improved process for the nickel-catalyzed hydrocyanation of alkyl 2-alkenoates is disclosed.

5 Claims, No Drawings

HYDROCYANATION OF CONJUGATED 2-ALKENOATES

FIELD OF THE INVENTION

This invention concerns a process for the hydrocyanation of conjugated 2-alkenoates, e.g., methyl 2-pentenoate (M2P) to produce a cyanoalkanoate, e.g., methyl 5-cyanovalerate (5CNV), wherein the reaction is catalyzed by a zero valent nickel catalyst in the presence of one or more promoters, preferably in the presence of a synergistic combination of promoters.

BACKGROUND OF THE INVENTION

The preparation of dinitriles, such as adiponitrile (AND), from mononitriloolefins, such as 3-pentenenitrile (3PN) or 4-pentenenitrile (4PN), utilizing zerovalent nickel catalysts has been accomplished with or without a promoter. Likewise, alpha-omega cyanoalkanoates, such as methyl 5-cyanovalerate (5CNV), have been prepared by hydrocyanation of non-conjugated alkenoates, such as methyl 3-pentenoate (M3P) or methyl 4-pentenoate (M4P), using a similar catalyst system. However, the hydrocyanation of the conjugated isomers, such as 2-pentenenitrile (2PN), has not been accomplished and 2PN is reported to be a catalyst inhibitor and yield loss. The process of this invention, i.e., the hydrocyanation of conjugated 2-alkenoates using zero valent nickel catalysts, was therefore unexpected in light of the effect of 2PN, and indeed previously unobserved.

U.S. Pat. No. 2,571,099, issued on Oct. 16, 1951 to Paul Arthur, Jr. et al., discloses the use of nickel carbonyl with or without the addition of a tertiary aryl phosphine or arsine. This process produces a relatively high percentage of undesirable polymeric products when applied to nonconjugated olefinic starting materials and a relatively poor yield in all cases.

U.S. Pat. No. 3,496,215, issued on Feb. 17, 1970 to W. C. Drinkard et al., discloses an improvement in nickel-catalyzed hydrocyanation wherein triarylphosphite ligands are utilized and carbonyl ligands are eliminated, thereby dramatically reducing polymer formation and generally increasing yield to desirable nitrile products.

The teaching of the use of a promoter in the hydrocyanation reaction appears in U.S. Pat. No. 3,496,217, issued on Feb. 17, 1970 to W. C. Drinkard et al. This patent discloses an improvement in hydrocyanation using a promoter selected from a large number of metal cation compounds with a variety of anions as catalyst promoters. The known organometallic compounds $(C_2H_5)_3Al_2Cl_3$ and $C_2H_5AlCl_2$ are also disclosed as promoters.

U.S. Pat. No. 3,496,218, issued on Feb. 17, 1970 to W. C. Drinkard, discloses a nickel hydrocyanation catalyst promoted with various boron-containing compounds, including triphenylboron and alkali metal borohydrides.

U.S. Pat. No. 3,925,445, issued on Dec. 9, 1975 to C. M. King et al., discloses zerovalent nickel hydrocyanation catalysts promoted with metal halides and organoboron compounds.

U.S. Pat. No. 3,852,325, issued on Dec. 3, 1974 to C. M. King, teaches that along with production of 3-pentenenitrile (3PN) in the hydrocyanation of butadiene, there is also obtained varying amounts of cis- and trans-2-pentenenitriles (C-2PN and T-2PN) and that these 2-pentenenitriles are found to be detrimental to catalyst efficiency in the hydrocyanation of 3-pentenenitrile or 4-pentenenitrile (4PN) to adiponitrile (AND).

U.S. Pat. No. 4,774,353 issued on Sept. 27, 1988, discloses a process for the preparation of dinitriles, e.g., AND, from nonconjugated unsaturated nitriles, e.g., 3PN or 4PN, in the presence of a zerovalent nickel catalyst and triorganotin catalyst promoters.

U.S. Pat. No. 4,874,884 issued Oct. 17, 1989, discloses that certain combinations of promoters, e.g., $B(C_6H_5)_3$ and $RAlCl_2$, where R is an alkyl group with 1-20 carbons, are synergistic, giving increased rates in the hydrocyanation of 3PN over that expected from either promoter alone.

U.S. Pat. No. 3,865,865 issued on Feb. 11, 1975, discloses the selective removal of 2-pentenenitrile (2PN) from a mixture of alkenyl nitriles. The patent states at column 1, lines 23-25, that "2-pentenenitrile ... are undesirable byproducts ... in that they are detrimental to catalyst efficiency." in nickel catalyzed hydrocyanation.

U.S. Pat. No. 3,564,040, issued on Feb. 16, 1971, discloses the removal of trans-2-pentenenitrile from a mixture of pentenenitriles. This patent states that "2PN is both detrimental to catalyst efficiency ... [and] a yield loss" (Col. 1, lines 55-68), thereby indicating that it cannot be directly hydrocyanated. The nickel catalyzed hydrocyanation of conjugated alkyl 2-alkenoates of the present invention was unexpected in view of the reports that 2PN inhibits hydrocyanation and is a yield loss, i.e., cannot be hydrocyanated.

SUMMARY OF THE INVENTION

This case concerns a process for the hydrocyanation of conjugated alkyl 2-alkenoates of the formula:

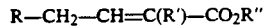

$$R-CH_2-CH=C(R')-CO_2R''$$

wherein R and R' are independently H, or alkyl or substituted alkyl (1-18 carbons), and R" is alkyl (1-18 carbons).

The process of this invention is comprised of the hydrocyanation of conjugated 2-alkenoates in the presence of zero valent nickel catalyst and in the presence of one or more Lewis acid promoters. Preferably a syngeristic combination of promoters, such as R'''AlCl_2 (R''' is alkyl, 1-18 carbons) and BPh_3 (Ph is phenyl) is employed in order to increase activity and minimize the amount of promoter and/or catalyst needed.

DETAILED DESCRIPTION OF THE INVENTION

The present invention concerns the use of a zero valent nickel catalyst, in combination with one or more Lewis acid promoters, most preferably two or more Lewis acids in synergistic combination, to accomplish the hydrocyanation of selected conjugated alkyl 2-alkenoates of the structure:

$$R-CH_2CH=C(R')CO_2R''$$

wherein R and R' are independently H, $C_1-C_{18}$ alkyl or substituted alkyl and R" is alkyl. A preferred mono-olefin is methyl 2-pentenoate (M2P). A preferred promoter combination is $C_{12}H_{25}AlCl_2$ and $BPh_3$.

By substituted alkyl is meant an alkyl with one or more hydrogen atoms replaced by an aryl group.

Use of the preferred combination of Lewis acid promoters in accordance with this invention provides a synergistic increase in the overall synthesis rate.

The catalysts employed for hydrocyanation herein are zerovalent nickel (Ni(O)) compounds substantially free of carbon monoxide. These compounds may be prepared in situ. Such catalysts are described in U.S. Pat. No. 4,774,353 which is incorporated herein by reference. These catalysts are described therein at Col. 3, lines 1–59. At lines 2–7 therein, they are described as ... "zerovalent nickel (Ni°) compounds free of carbon monoxide which may be preformed or prepared in situ and include nickel compounds containing ligands such as alkyl or aryl groups (either of which groups can contain up to 18 carbon atoms) phosphines, arsines, stibines, phosphites, arsenites, stibites and mixtures thereof."

An especially preferred group of these Ni(O) compounds described in U.S. Pat. No. 4,774,353 have the general structure:

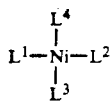

wherein $L^1$, $L^2$, $L^3$ and $L^4$ are neutral ligands which may be the same or different and have the formula P(XYZ) wherein X and Y are selected from the class consisting of R and OR, and Z has the formula OR, wherein the three R's may be the same or different, and wherein R is selected from the class consisting of alkyl and aryl groups containing up to 18 carbon atoms with aryl being preferred.

An especially desirable class of R's is:

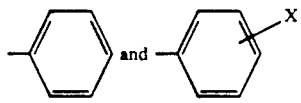

where X is selected from the class consisting of Cl, $OCH_3$ and $CH_3$. The R's may be cojoined. The preferred neutral ligands of this group are the aryl phosphites such as triphenyl phosphite, tri(m- and p-chlorophenyl) phosphite, tri-(m- and p-methoxyphenyl) phosphite and tri-(m- and p-tolyl) phosphite and mixtures thereof. One or more of the neutral ligands may become dissociated from the nickel during the reaction.

A particularly preferred group of monovalent nickel catalysts is described in U.S. Pat. No. 3,903,120 issued on Sept. 2, 1975, which can be described by the general formula $NiL_4$ where L is a neutral ligand such as a triaryl phosphite of the formula $P(OAr)_3$ wherein Ar is an aryl group of up to 18 carbon atoms.

The promoters most useful in the practice of this invention can be selected from a wide variety of Lewis acid compounds, either singly or in combination. Preferred promoter combinations include those described in U.S. Pat. No. 4,874,884. An especially preferred Lewis acid combination is $BPh_3$ and $C_{12}H_{25}AlCl_2$.

EXAMPLES

The following Examples illustrate the invention. The mixtures were heated in a thermostatically controlled oil bath. HCN was delivered to the flask as an HCN/$N_2$ gas mixture by bubbling dry nitrogen gas through liquid HCN at 0° C. (maintained in an ice bath); this provides a vapor stream which is about 35% HCN (vol/vol). The rate of nitrogen gas flow determines the rate of HCN delivery. Sample analysis was carried out by gas chromatographic (GC) analysis with a cross-linked methyl silicon capillary column (25 m; 0.2 mm id). Conversions are the sum total of all penteneoate isomers converted to 3-, 4- and 5-cyanovalerate. Product distribution is the percent 5-cyanovalerate in the combined 3-, 4- or 5-cyanovalerate. The rate of hydrocyanation was judged by analysis of GC changes.

The following example reveals that the reaction is not completely inhibited by high concentrations of M2P as is known to occur for 2PN.

EXAMPLE 1

A glass reaction vessel was charged with 50% (v/v) tetrakis(tri-m-p-tolylphosphite)nickel(O)/toluene (8.0 mL; 2 mmol Ni), tri-p-tolylphosphite (2.0 mL; 7 mmol), methyl 3-penteneoate (20 mL; 160 mmol), $Ph_3SnCNBPh_3$ (0.50 g; 0.8 mmol), and $BPh_3$ (0.20 g; 0.8 mmol) under nitrogen gas. The mixture was heated to 50° C. and HCN fed with a nitrogen flow of 6.5 mL/min. After 1 hour, the temperature was raised to 60° C. and the flow reduced to 5 mL/min for another hour. Then the temperature was raised to 75° C. for 4 hours with a nitrogen flow of 3 mL/min and finally the temperature raised to 85° C. and the flow reduced to 2.5 mL/min until the reaction stopped due to deactivation of the catalyst.

After only 0.5 hours, significant isomerization of methyl 3-penteneoate to methyl 2-penteneoate had already occurred. Methyl 2-penteneoate continued to grow throughout the reaction. At 6 hours, when the temperature was being raised to 85° C., about 22% of the penteneoates had been converted to cyanovalerate, with a distribution of 1.4% methyl 4-penteneoate, 27.9% methyl 3-penteneoate, and 70.7% methyl 2-penteneoate. The reaction stopped after several more hours at 27% conversion, 91.1% distribution to 5-cyanovalerate, and a penteneoate distribution of 1.1% methyl 4-penteneoate, 24.5% methyl 3-penteneoate, and 74.4% methyl 2-penteneoate.

Though the reaction slowed, it is clear that hydrocyanation was proceeding in the presence of >60% methyl 2-penteneoate and that methyl 2-penteneoate is not inhibiting the reaction.

EXAMPLE 2

In this example it is clear that though starting with methyl 3-penteneoate (M3P), some methyl 2-penteneoate (M2P) is made and consumed A glass reaction vessel was charged with 50% (v/v) tetrakis(tri-m-p-tolylphosphite)nickel(O)/toluene (8.0 mL; 2 mmol Ni), tri-p-tolylphosphite (4.0 mL; 14 mmol), methyl 3-penteneoate (20 mL; 160 mmol), $C_{12}H_{25}AlCl_2$ (1.5 mL of 1.0 M in toluene; 1.5 mmol) under nitrogen gas. The mixture was heated to 50° C. and HCN fed with a nitrogen flow of 7 mL/min for 6 hours and then at 60° C. for 1 hour more. The temperature was then raised to 80° C. and the flow reduced to 2.5 mL/min for 15 hours.

Isomerization to M2P was much slower though still significant with this very active promoter. The following table reveals that methyl 2-penteneoate was made and consumed. In this case, the % methyl 2-penteneoate is with respect to the sum of the penteneoates and the cyanovalerates, and distribution of 5 cyanovalerates is with respect to the sum of all cyanovalerate produced.

| Time (hrs) | Conversion (of all penteneoates) | Distribution (% 5-cyanovalerate) | % Methyl 2-penteneoate |
| --- | --- | --- | --- |
| 1.5 | 11 | 94 | 3.5 |
| 5.5 | 52 | 90 | 7.1 |
| 6.75 | 65 | 88 | 8.0 |
| 7.5 | 72 | 88 | 8.3 |
| 22.0 | 89 | 88 | 6.3 |

EXAMPLE 3

Starting with methyl 2-penteneoate, a synergistic combination of promoters was added to increase activity.

A glass reaction vessel was charged with 50% (v/v) tetrakis(tri-m-p-tolylphosphite)nickel(O)/toluene (8.0 mL; 2 mmol Ni), tri-p-tolylphosphite (4.0 mL; 14 mmol), methyl 2-penteneoate (20 mL; 160 mmol), $C_{12}H_{25}AlCl_2$ (1.5 mL of 1.0 M in toluene; 1.5 mmol) and $BPh_3$ (0.25 g; 1.0 mmol) under nitrogen gas. The mixture was heated to 75° C. and HCN fed with a nitrogen flow of 2.5 mL/min until the catalyst was deactivated (about 4 hours). 11.5% conversion of penteneoates occurred with a 92.4% distribution to 5-cyanovalerate. The penteneoate and cyanovalerate distribution in the final product mixture was as follows: 0.7% methyl 4-penteneoate, 14.1% methyl 3-penteneoate, 73.7% methyl 2-penteneoate, 0.2% 3-cyanovalerate, 0.7% 4-cyanovalerate and 10.6% 5-cyanovalerate.

A similar reaction where the promoter was only $ZnCl_2$ (no Al or B promoter) produced a trace of 5-cyanovalerate.

A similar reaction with methyl 2-penteneoate replaced by 2-pentenenitrile failed to produce detectable quantities of adiponitrile, or other dinitriles.

It is to be understood that the invention herein is not to be limited to the embodiments exemplified but only by the claims appended hereto.

What is claimed is:

1. A process for the hydrocyanation of alkyl 2-penteneoate mono-olefins of the form:

$$CH_3-CH_2-CH=C(H)-CO_2R''$$

where $R''$ is alkyl of 1 to 18 carbon atoms, conducted in a liquid phase, in the presence of a zero valent nickel catalyst free of carbon monoxide, and in the presence of one or more Lewis acid promoters, wherein the hydrocyanated product distribution contains at least about 88% alkyl 5-cyanovalerate.

2. The process of claim 1 conducted in the presence of a synergistic combination of two or more Lewis acid promoters.

3. The process of claim 1 wherein the Lewis acid promoter used is $R'''AlCl_2$ where $R'''$ is an alkyl of 1 to 18 carbon atoms.

4. The process of claim 2 wherein the synergistic combination of promoters comprises $BPh_3$ and $C_{12}H_{25}AlCl_2$.

5. The process of claim 1 wherein the mono-olefin is methyl 2-pentenoate.

* * * * *

UNITED STATES PATENT AND TRADEMARK OFFICE
CERTIFICATE OF CORRECTION

PATENT NO. : 5,087,723

DATED : FEBRUARY 11, 1992

INVENTOR(S) : RONALD JAMES McKINNEY

It is certified that error appears in the above-identified patent and that said Letters Patent is hereby corrected as shown below:

Col. 2, line 5, replace "AND" with -- ADN --.

Signed and Sealed this

Twenty-seventh Day of April, 1993

Attest:

MICHAEL K. KIRK

Attesting Officer     Acting Commissioner of Patents and Trademarks